(12) United States Patent
Tan

(10) Patent No.: US 9,125,877 B2
(45) Date of Patent: Sep. 8, 2015

(54) USE OF KAURANES COMPOUNDS IN THE MANUFACTURE OF MEDICAMENT

(76) Inventor: Wen Tan, Corpus Christi, TX (US)

( * ) Notice: Subject to any disclaimer, the term of this patent is extended or adjusted under 35 U.S.C. 154(b) by 997 days.

(21) Appl. No.: 11/596,514

(22) PCT Filed: May 19, 2004

(86) PCT No.: PCT/CN2004/000508
§ 371 (c)(1),
(2), (4) Date: Nov. 13, 2006

(87) PCT Pub. No.: WO2005/110383
PCT Pub. Date: Nov. 24, 2005

(65) Prior Publication Data
US 2010/0179097 A1    Jul. 15, 2010

(51) Int. Cl.
*A61K 31/19* (2006.01)
*A61K 31/191* (2006.01)
*A61K 31/045* (2006.01)
*A61K 31/047* (2006.01)

(52) U.S. Cl.
CPC ............... *A61K 31/19* (2013.01); *A61K 31/045* (2013.01); *A61K 31/047* (2013.01); *A61K 31/191* (2013.01)

(58) Field of Classification Search
None
See application file for complete search history.

(56) References Cited
U.S. PATENT DOCUMENTS
2004/0081712 A1* 4/2004 Hermansen et al. .......... 424/757

FOREIGN PATENT DOCUMENTS
WO    WO 0247675 A    6/2002
WO    WO 02060419 A    8/2002

\* cited by examiner

*Primary Examiner* — Bethany Barham
*Assistant Examiner* — Barbara Frazier
(74) *Attorney, Agent, or Firm* — Osha Liang LLP

(57) ABSTRACT

The invention relates the pharmaceutical use of kaurene compounds of formula (1) in treating and preventing coronary disease, stroke, cerebral ischemia and arrhythmia etc. The said compounds also have significant protecting effects against cerebral ischemic infarction.

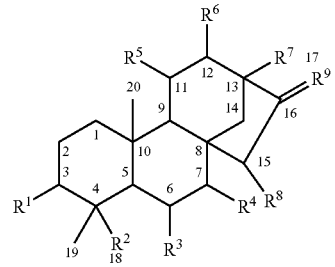

Wherein
$R^1$: hydrogen, hydroxyl or alkoxy
$R^2$: carboxyl, carboxylate, acyl halides, aldehyde, methylhydroxyl, and ester, acylamide, acyl or ether group hydrolysable to carboxyl.
$R^3, R^4, R^5, R^6, R^8$: independently, oxygen, hydroxyl, methylhydroxyl, and ester or alkyloxymethyl group hydrolysable to methylhydroxyl,
$R^7$: methyl, hydroxyl, and ester or alkyloxymethyl hydrolysable to methylhydroxyl,
$R^9$: methylene or oxygen.

8 Claims, No Drawings

USE OF KAURANES COMPOUNDS IN THE MANUFACTURE OF MEDICAMENT

FIELD OF INVENTION

The invention relates the pharmaceutical use of kaurene compounds, in particular compound A and B.

BACKGROUND OF INVENTION

Coronary disease is one of the most prevalent diseases caused by coronary stenosis or obstruction. It can result in angina pectoris, arrhythmias, myocardial ischemia or infarct and heart failure. Myocardium injury also occurs during reperfusion when the obstructed coronary are suddenly reopened by clinic procedures such as coronary angioplasty, stent or thrombolytic therapy. Reperfusion can results in serious arrhythmias and cardiac failure. A number of drugs have been developed for treating myocardium injury or arrhythmia caused by ischemia or reperfusion. However, the therapeutic benefits of these drugs are limited due to either toxicity or poor efficacy.

Brain stroke including either ischemic stroke or hemorrhagic stroke is one of the leading causes of death in US. It can lead to neuronal injury and cerebral dysfunction as results of ischemia and hypoxia. Brain ischemia may also occur during head trauma or hemorrhagic shock. Since the metabolite rate and oxygen consumption are much higher in brain and central nerve system comparing to other issues, they are more susceptible to ischemia or hypoxia, which may lead to death or irreversible injury. It is desirable to find better medicine to protect against cerebral ischemic injury and preserve brain function.

Compounds of nature origin have been proved to be efficacious and less toxic. For instance, nature digitalis glycoside now plays important roles in treating heart failure and arrhythmia. It has to be used with great caution, however, because the toxic dose of digitalis is very close to its therapeutic dose. To further improve the drug therapy in treating of coronary disease, arrhythmia, heart failure and cerebral stroke, an important approach is discovery more desirable drug from nature source.

Kaurene compounds of formula (I) have been widely studied for their possible biological and pharmacological effects. Most of the studies in art concern their roles in metabolite mechanism. (Kinghorn, A D. 2002, Stevia, by Taylor & Francis Inc.) For instance, it was reported that the said compounds affects cellular metabolite, glucose absorption in intestine and carbohydrate metabolism, energy metabolism in mitochondria of hepatic cells, and metabolite of carbohydrate and oxygen in renal cells. It was also reported that the said compounds cause vasodilation and hypotension. However, the effects of said compounds on cardiac function received litter attention. No study in art has documented the effects of said compounds on cardiac and cerebral ischemia or arrhythmia and myocardium contractility.

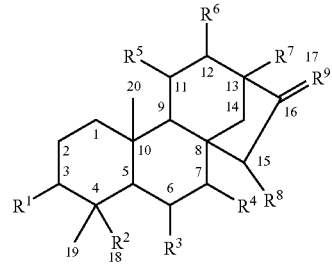

wherein
ii. $R^1$: hydrogen, hydroxyl or alkoxy
iii. $R^2$: carboxyl, carboxylate, acyl halides, aldehyde, methylhydroxyl, and ester, acylamide, acyl or ether group hydrolysable to carboxyl.
iv. $R^3$, $R^4$, $R^5$, $R^6$, $R^8$: independently, hydrogen, oxygen, hydroxyl, methylhydroxyl, and ester or alkyloxymethyl group hydrolysable to methylhydroxyl
v. $R^7$: methyl, hydroxyl, and ester or alkyloxymethyl hydrolysable to methylhydroxyl,
vi. $R^9$: methylene or oxygen.

Natural stevioside has a kaurene skeleton as aglycone; it has a sweetening potency 300 times that of sucrose and has long been used as food sweetener in many countries. It has been shown that stevioside can lowering blood sugar (Gregersen S et al., 2004) and lowering blood pressure (Chen P at el., 2000), but has no effects on heart rate and other parameters related to cardiac function (Hseih M H et al., 2003). In animal studies, it has been shown that stevioside is diuretic, stimulating the secretion of insulin (Jeppesen P B, 2000) and inhibition of energy metabolite in mitochondria (WHO, 1999). However, the possible role of stevioside on cardiac or cerebral ischemia has not been reported previously.

Two well-known kaurene compounds related to stevioside are compound A (as shown in formula (II)) and compound B (as shown in formula (III)).

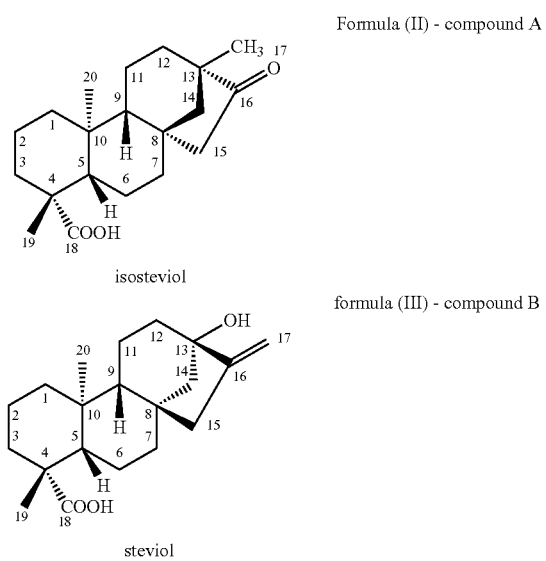

As aglycone of stevioside, compound B has received great attention and its biological and pharmacological effects have been reported from various animal studies. These includes stimulating the secretion of insulin, inhibiting the absorption, transport, metabolite of carbohydrates, inhibiting energy metabolite (Jeppesen b P, 2000); and inhibiting tubular transport of some xenobiotics and facilitating the excretion of sodium and water in renal. (Chatsudthipong et al., 2001). It was also shown that compound B has certain mutagenic effects (Puzzuto J M et al 1984). However, in the prior art, no study has reported of any effects of compound B on normal cardiac function or of any therapeutic effects on cardiac ischemia and reperfusion injury, arrhythmia, and brain stroke. Compound B can not be catalyzed and cleaved from stevioside by peptic enzymes, but may be by the action of bacteria in animal intestine, then be absorbed. Stevioside can not be metabolized into compound B or A when administered by intravenous injection. Therefore, Results obtained from stevioside studies may not useful in interpreting the effects of its aglycone, i.e. compound B or compound A.

Compound A and compound B have relatively low biotoxicity. For compound A, the minimum oral lethal dose is 5060 mg/kg in mice and 3160 mg/kg in rats, the median lethal dose ($LD_{50}$) by intravenous injection is 503 mg/kg in rats. The major symptoms of toxicity at lethal dose are vasodilation and renal failure (Zhongguo et al., 1994). For compound B, the oral median lethal dose ($LD_{50}$) is 1500 mg/kg in rats (WHO, 1999). Compound A and compound B is relatively safe comparing with common drugs according to the lethal doses.

To our knowledge in art, compound A and compound B have not been used in pharmaceutical compositions for therapeutic use.

In short, coronary disease and brain stroke pose a serious threat to human health. Although drugs of natural origin available are efficacious in treating these diseases, for instance digitalis, but their clinic benefits are limited due to toxicity, Kaurene compounds of formula (I) represent a class of natural compounds, some of which have subjected to a widely studies as a sweetener and revealed a good safety profile. However, the possible therapeutic roles of kaurene compounds on coronary disease or brain stroke have not been determined previously. To overcome the shortcomings, in the invention we have first determined and reported the therapeutic use of kaurene compounds of formula (I) and its preferred compounds in treatment of cardiac and cerebral ischemic diseases by utilizing well-characterized rat models and by more specifically and thoroughly screening and testing.

DESCRIPTION

Object of the Invention

The object of the invention is to provide a more desirable methods or medication from less toxic natural kaurene compounds for treating and preventing coronary disease and brain stroke. The said methods or medication shall be more advantageous than current drugs in term of efficacy and safety profiles in treating tissue and organ ischemic diseases in clinic practice.

It is also an object of the invention to provide kaurene compounds allowing treating heart failure.

It is also an object of the invention to provide kaurene compounds allowing treating arrhythmia.

The object of the invention can be achieved by using kaurene compounds of the invention in manufacture of pharmaceutical compositions for treatment of tissue or organ ischemic diseases.

The object of the invention can also be further achieved by using the following techniques and methods.

The abovementioned tissue and organ ischemic diseases include cardiac and cerebral ischemic disease.

The abovementioned tissue and organ ischemic disease include damage or necrosis of extremity of limbs, retina, optic nerves and kidneys.

The abovementioned cardiac and cerebral ischemia diseases include coronary disease, brain stroke, cerebral ischemic injuries and ischemic-reperfusion injury.

The said coronary disease includes angina pectoris or acute cardiac infarction.

The said brain stroke includes ischemic stroke and hemorrhage stroke.

The said cerebral ischemic injury includes trauma, hemorrhagic shock, or reduced blood supply due to arteriosclerosis or stenosis.

The said ischemia-reperfusion injury is caused by coronary angioplasty, coronary thrombolytic therapy, drugs induced coronary dilation, extracorporeal circulation in cardiac surgery, cerebral thrombolytic therapy.

The object of the invention can be achieved by using kaurene compounds of the invention in manufacture of pharmaceutical compositions for treatment of heart failure. The object of the invention can be further achieved by using the following techniques and methods.

The said heart failure includes congestive heart failure or heart failure due to decrease in cardiac contractility and cardiac output.

The object of the invention can be achieved by using kaurene compounds of the invention in manufacture of pharmaceutical compositions for treatment and prevention of arrhythmia.

The object of the invention can also be further achieved by using the following technologies and methods.

The abovementioned arrhythmia is caused by cardiac ischemia and reperfusion.

The said arrhythmia includes ventricular, super ventricular or atria arrhythmia according to their origin.

The said arrhythmia includes ventricular tachycardia or ventricular fibrillation.

According to the invention, the said kaurene compounds have a general structure as in formula (I):

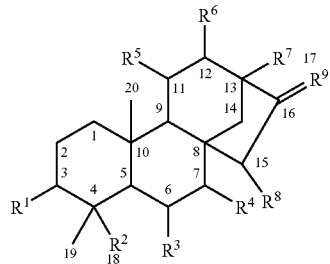

Wherein
ii. $R^1$: hydrogen, hydroxyl or alkoxy
iii. $R^2$: carboxyl, carboxylate, acyl halides, aldehyde, methyl-hydroxyl, and ester, acylamide, acyl or ether group hydrolysable to carboxyl.
iv. $R^3$, $R^4$, $R^5$, $R^6$, $R^8$: independently, oxygen, hydroxyl, methylhydroxyl, and ester or alkyloxymethyl hydrolysable to methylhydroxyl,
v. $R^7$: methyl, hydroxyl, and ester or alkyloxymethyl hydrolysable to methylhydroxyl.
vi. $R^9$: methylene or oxygen.

The said kaurene compounds, wherein compounds of formula (I) is the compound A presented in formula (II)

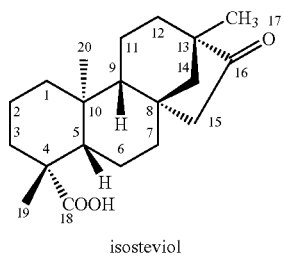

isosteviol

The said kaurene compounds, wherein compounds of formula (I) is the compound B presented in formula (II)

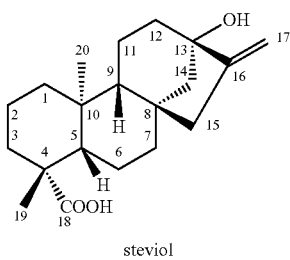

steviol

The said kaurene compounds, wherein the carboxylate is alkaline-earth metal or basic metal or ammonium carboxylate.

The kaurene compounds noted above, wherein the said medications or pharmaceutical compositions include tablets, capsules, granule, injection liquid, suppository, ointment and any slow or controlled released dosage forms administered via oral, injection, implant or catheter intervention etc.

The objects above are achieved by the invention and the benefits and advantages of the invention are apparent from the following description of the preferred embodiments thereof and from the claims.

DESCRIPTION OF THE INVENTION

The invention discloses the effects of kaurene compounds as in formula (I) in treating cardiac and cerebral ischemia, arrhythmia and cardiac failure. The compounds in formula (1) represent a class of natural, synthetic or semi-synthetic compounds. Many of these compounds has been known to public (Kinghorn A D, 2002, p 86-137; Sinder B B, et al., 1998; Chang F R et al., 1998; Hsu, F L et al., 2002). Compounds in formula (I) may have one or more asymmetric centers and may exist in different stereo isomers.

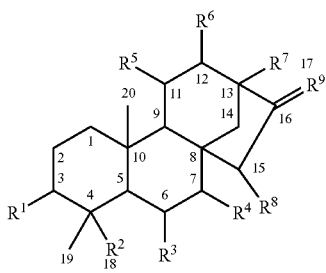

Wherein
ii. $R^1$: hydrogen, hydroxyl or alkoxy
iii. $R^2$: carboxyl, carboxylate, acyl halides, aldehyde, methylhydroxyl, and ester, acylamide, acyl or ether group hydrolysable to carboxyl.
iv. $R^3$, $R^4$, $R^5$, $R^6$, $R^8$: independently, oxygen, hydroxyl, methylhydroxyl, and ester or alkyloxymethyl hydrolysable to methylhydroxyl.,
v. $R^7$: methyl, hydroxyl, and ester or alkyloxymethyl hydrolysable to methylhydroxyl.
vi. $R^9$: methylene or oxygen.

A group of preferred compounds is presented in Formula (I'). The said compounds have kaurene structure, with substitutions adjacent to carbon 13, and derivatives at carbons 17 and 18. These said compounds may have multiple asymmetric centers, and exist as different stereo-isomers or dia-stereo-isomers. The absolute configuration related the position 8 and 13 are (8R,13S)- or (8S,13R).

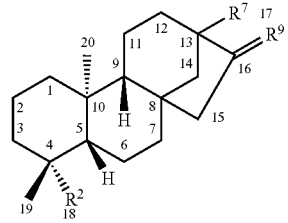

Wherein:
ii. $R^2$: carboxyl, carboxylate, aldehyde, methyl-hydroxyl, methyl ester, acyl methyl, acyl halides.
iii. $R^7$: methyl, methyl-hydroxyl, or methyl ether.
iv. $R^9$: methylene or oxygen.

Compound A can be obtained by acidic hydrolysis of natural stevioside. Compound B is the aglycone of stevioside which is compound B glycoside. Compound A and B are isomers. Compound B can be obtained from stevioside by chemical reactions of hydrolysis and oxidation or by catalysis reactions of bacteria within animal intestine.

Formula (II) - compound A

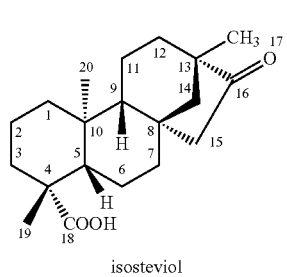

isosteviol

Formula (III) - compound B

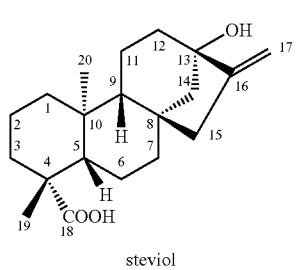

steviol

Compound A, molecular formula, $C_{20}H_{30}O_3$; chemical name: (4α,8β,13β)-13-methyl-16-oxo-17-norkauran-18-oic acid; It also named isosteviol, ent-16-ketobeyran-18-oic acid.

The said compound is a tetraditerpene with kaurane structure, wherein, the absolute configuration of asymmetric carbons are: (4R,5S,8R,9R,10S,13S)—, a substituted methyl group at carbon 13, a carbonic group at carbon 16 and a carboxyl group at carbon 18. (Rodrigues et al., 1988)

Compound B, molecular formula, $C_{20}H_{30}O_3$; chemical name: ent-13-hydroxykaur-16-en-18-oic acid, it also named as steviol. The said compound is also a tetraditerpene with kaurene skeleton, wherein, the absolute configuration of chiral carbons are: (4R,5S,8R,9R,10S,13S)—, a substituted hydroxyl group at carbon 13, a methylene group attached by a double bond adjacent to carbon 16 and carboxyl group at carbon 18. (Rodrigues et al., 1993)

Compound A or B may also exist as carboxylate at 18 position, wherein the carboxylate are sodium and basic metals or chloride and halogen. Both compound A and B have the kaurene structure and are kaurene compounds. Compound A is the more preferred compound in this invention. This invention discloses that compound A or B has similar therapeutic effects in treating and preventing ischemic myocardium injury and arrhythmia caused by ischemia or reperfusion and preserving and enhancing the contractile function of ischemic myocardium. It may be inferred that all the other compounds of formula (I) also have the same kind of therapeutic effects as did of compound A. It is reported that large amount of compound B may be mutagenic under certain condition in vitro, therefore, compound A is more preferable comparing with compound B, to be used in pharmaceutical medication.

This invention also discloses a structure-activity relationship of compounds of formula (1). By comparing the testing results from compound A and compound B, It can be inferred that the above therapeutic effects reside in the basic structure of kaurene skeleton. Substitution of some radicals on the kaurene skeleton (such as at carbon 13 and 17) or changing of the stereo-configurations (such as at carbon 8 and 13) do not change the efficacy but only the potency of the compounds. it again indicates that all the other compounds in formula (I) may have the same kind of therapeutic effects as did of compound A in treatment of cardiac ischemia, cerebral ischemia, arrhythmia and in enhancement of cardiac function.

The invention teaches methods of use compounds of formula (I) to form salts, to preparing pharmaceutical composition and to administer to a patent in need. Compound A and B can form pharmaceutical acceptable salts with materials, such as basic metals (e.g. sodium) and halogen in order to increase their water solubility. Compound A and B can be formulated with suitable pharmaceutical carriers and solvents into solid or liquid dosage forms which include tablets, capsules, controlled or sustained released forms, injection preparation, suppository, trans dermal patch, ointment and etc. These suitable dosage forms for long or short term used can be administered via routes of oral, intravenous, rectum, vagina or sublingual, or via catheter intervention into vein or artery.

The invention discloses an effective dosage range of compound A from 0.5 to 4.0 mg/kg and a no obvious toxicity dose of up to 40 mg/kg administered intravenously. The previously reported acute toxicity of compound A is very low, the median lethal dose ($LD_{50}$)=650 mg/kg by intravenous injection. It estimates a safety dose range for clinic use may be around 0.1 to 0.2 mg/kg. Other compounds of formula (I), such as compound B, also show relatively small effective dose and large safety dose. In this invention, the effective dose of compound B is between 2 to 8 mg/kg, in a reported acute toxicity study (WHO, 1999), the median lethal dose ($LD_{50}$) of compound B was 1500 mg/kg. In addition, compound B has similar therapeutic effects as compound A, such as improvement of contractile function in ischemic heart, protection and amelioration the damage of myocardium during ischemia and reperfusion, and anti-arrhythmia etc. In general, to achieve similar effects requires a higher dose of compound B than compound A.

The invention reveals a minimum effective dose of both compound A and B. Since compound A has a large median lethal dose and relatively safe, in the past, researchers usually started with larger doses of compound A in therapeutic studies, but overlooked the effects of small doses. In the invention, the effective doses for compound A and B were only 1 to 2 mg/kg in rats. The equivalent doses for pigs are 0.2 to 0.4 mg/kg, and for human are 0.1 to 0.2 mg/kg based on body surface area. The effective dose of compound A and B in the invention is far less than the dose reported in published data. The minimum doses of compound A and B used in published reports in vivo are respectively 25 mg/kg of compound A in rats (Liu, C J et al., 2001), 250 mg/kg of compound B in hamsters (Wasuntarawat C, 1998). In human, stevioside at doses of 250 mg and 500 mg, three times daily were used for anti-hypertension studies (Chen P et al., Hsieh M H et al., 2003). It equals to administer the amount of compound B orally 80-160 mg, corresponding to 1.2 to 2.4 mg/kg in human, base on the molecule ratio of compound B in stevioside, if it can be elevated.

Studies published in art have failed to demonstrate that compounds of formula (I) in particular compound A and B have any therapeutic effects against cardiac and cerebral ischemia as did in the invention. This may be attributed into two aspects: 1, the dosages of the compounds A or B used in these studies were too high; 2, a suitable or effective animal ischemic model was not chosen to use. The invention is completely different than the previous studies in this regard.

It was reported that a large dose of compound A (25 mg/kg) results in vasodilation and lowering of arterial pressure administered by intraperitoneal in rats (Lucy., et al. 2001). In this invention, a small dose of compound A (1 mg/kg) administered by intravenous in rats observed no such hypotension effect, but the protective effects against cardiac and cerebral ischemia. This indicates that the underlying mechanism of the protective effects of the inventions is different than the hypotensive effects of the previous report. In addition, the difference in the effective doses between the invention and previous report can not be attributed to the routes of administration of compound A, i.e. intraperitoneal (in previous report) v.s intravenous (in the invention). The results of acute toxicity studies of compound A in rats are similar when administered by intravenous or intraperitoneal (the $LD_{50}$ is 503 mg/kg and 617 mg/kg respectively,) (zhonggou et al., 1994), which indicates there is no different in absorbing and utilizing the compound A in rats when administered via either intravenous or intraperitoneal. In addition, the same study also reported that the $LD_{50}$ is 3160 mg/kg when administered by oral in rats which is a far larger than above two doses of $LD_{50}$.

The therapeutic effects of compounds A or B above mention may involve in multiple mechanisms. Previous reports showed that hypotensive effects of compound A may involve potassium channels of myocyte membrane (Wang, K L et al, 2004), while the potassium channels potassium channels were not involved in a stimulating effects of compound A on insulin secretion (Jeppesen P B., et al, 2000). This invention reveals that compound A and B play protective roles in ischemic mitochondria, which can only be partially blocked by 5-OH-decdanoate, a potassium ATP channel blocker.

The objects of the invention are met by utilizing a well-characterized ischemia-reperfusion rat model which is suitable for reproduce related clinic pathology and symptoms. Cardiac deficiency, arrhythmia, and myocardium injuries were evidence during coronary occlusion or reopen in rats, which are correlating well with the similar clinic findings during cardiac attack and coronary reperfusion caused by thrombolytic therapy or angioplasty.

The said animal model is also suitable for arrhythmia studies. Since ischemia-reperfusion per se involves in multiple pathological processes, the arrhythmia reproduced in the invention may correlate to the clinic arrhythmia of various underlying mechanisms.

The said animal model is also suitable for study of cardiac deficiency, in which decreased cardiac output as results of regional myocardium ischemic injuries will eventually leads to cardiac failure. This correlates well with clinic cardiac deficiency or congestive heart failure characterized by reduced cardiac output.

As noted above, the invention discloses a method of treating and preventing of coronary diseases, heart failure, arrhythmia and brain stroke comprising use kaurene compounds as active ingredient in pharmaceutical compositions. Among the said compounds, the preferable compound is compound B, the aglycone of stevioside; the more preferable compound is compound A, a product of acidic hydrolysis of stevioside. The invention disclose a method of protecting against ischemia and reperfusion injury and enhancing cardiac contractile function, against arrhythmia and reduce the risk of ventricular tachycardia and fibrillation comprising use of the said compounds of the invention. The invention also demonstrates, by utilizing a brain ischemic model, the use of said compounds in protection against cerebral stroke and ischemic injury and in preserving cerebral function during ischemia.

Major advantages of the invention include the aspects of the following:

1, the therapeutic use of the kaurene compounds include compound A and B in treatment and prevention of cardiac and cerebral ischemic diseases, arrhythmia and heart failure. The said compounds are originated from a natural plant consumed by human over years. In particular, compound A and B may have great clinic potential due to a relative high potency and high safety dose as well as due to both therapeutic and prophylactic nature.

2, the invention first examines the effects of compounds of formula (1) on the ultra structure of cardiac myocytes. The invention, by combining morphological and functional methods, reproduces the pathology of myocardium ischemia in animal model and demonstrates that the said compounds, in particular compound A and B, are therapeutically effective in protecting against ischemic myocardium and mitochondria injuries, reducing the infarction area, preserving and enhancing cardiac contractile function and reducing the risk of sever arrhythmia during ischemia.

3, the invention first discloses a significant positive inotropic effect of kaurene compound on myocardium, which can diminish the reduction of contractile function or preserve the function toward normal during ischemia. In clinic, cardiac failure or congestive heart failure characterized by a reduction of cardiac output can be treated by using Compound A and B. The unique advantage of compounds of formula (I) is that they reduce the risk of sever arrhythmia and ameliorate myocardium injury during ischemia, while enhancing the contractile function. Kaurene compounds has much better therapeutic index over digitalis glycoside, Digitalis glycoside are commonly used a class of positive inotropic agents, while it also worsens the ischemic myocardium, increase the infarct size and induce sever arrhythmia when over dose. In light of the shortcomings, the invention of therapeutic use of kaurene compounds is of important clinic significance.

4, the invention discloses a significant protective effect against reperfusion injury. Cardiac reperfusion injury may occur in clinic procedures including angioplasty, stent, by-pass surgery, thrombolytic therapy; drug induced coronary dilation, and extracorporeal circulation etc. The underlying mechanisms may involve excess oxygen radicals, overload calcium and other factors. Reperfusion may lead to damage of myocardium, cardiac failure, lethal arrhythmia such as ventricular tachycardia and fibrillation as been manifested in the invention. The invention reveals that use of compound A and B can significantly ameliorate myocardium damage, reduce the risk of ventricular tachycardia and fibrillation caused by reperfusion and preserve the cardiac function. Therefore, the said kaurene compounds, in particular compound A and B, can be used as a therapeutic medication in treatment and prevention the reperfusion injuries caused by the procedures mentioned above as well as by spontaneous coronary reopening from spasm or thrombi.

5, the invention discloses the use of kaurene compounds in treating of arrhythmia. The frequency of occurrence and the duration of ventricular tachycardia and fibrillation in rats caused by coronary ischemia and reperfusion were significantly reduced by administering compound A or B. Compounds of formula (I), in particular compound A and B of the invention can be used as therapeutic drugs in treatment of arrhythmia caused by ischemia and reperfusion, and also the arrhythmia caused by other mechanisms, since the ischemia and reperfusion model per se involves in multiple pathological processes.

6, the invention discloses the use of kaurene compounds in protection against brain stroke or injury. The basic life functions, such as respiratory function, lose shortly in mice after cessation of blood supply to the head. However, the duration of maintenance of respiratory function after the cessation of blood supply is significantly prolonged in mice treated with kaurene compounds, either compound A or B. This result indicates kaurene compounds has significant therapeutic effects in treatment and prevention of brain stroke (including both ischemic and hemorrhagic stroke), cerebral ischemia or injury caused by failure of systemic circulation, or head trauma.

7, the invention discloses a method of use kaurene compounds in protecting cardiac or cerebral tissues against ischemia. It is also directed to a methods of use the said compounds in treating and preventing ischemic necrosis in the extremity of limbs as results of diabetics or peripheral arterial abnormalities, ischemia of retina and optic nerves, and ischemia of kidneys (e.g. acute renal failure) etc.

8, the invention shows a non-linear dose-response relationship between said kaurene compounds and the said effects there is no further increase in the said effects when the dose administered beyond a certain range. At an extremely high dose, the said effects may be abrogated. In a pig study in the invention, a balloon-tip catheter was intervened into left anterior descending coronary artery (LAD) under the guidance of X-ray angiograph. Coronary ischemia and reperfusion was reproduced by inflating or deflating the balloon. Sever arrhythmia induced by ischemia was effectively prevented in pig pretreated with kaurene compounds (e.g. compound A) at a small dose which per se had no observable effects on heart before ischemia. When an extremely high dose (20 times more) of compound A was administered via LAD, there is a significant decrease in cardiac contractile function. This result indicates that kaurene compounds may act on different receptors or cell targets with deferent affinity. Kaurene compounds at this large dose may initiate an opposite or undesired effect which can diminish or override the therapeutic effects mentioned above.

9, the invention is also directed to a method of both therapeutic and prophylactic use of kaurene compounds. Since pretreatment of animals with compound A or B can effectively protect cardiac and cerebral against ischemia and reperfusion injuries, and in addition kaurene compounds has good safety profile, the said compounds are suitable for both therapeutic and prophylactic medication for coronary or cerebral arteries diseases. In clinic, compound A may be administered repeatedly for long-term as a prophylactic medicine for the patients who may be at the risk of angina pectoris, cardiac attach, cerebral ischemia or emboli, or sever arrhythmia as well as for the patents who may be at the risk of reperfusion injury.

In summary, the invention relates the methods of using kaurene compounds of formula (I) as active ingredients in various pharmaceutical compositions in treatment and prevention of coronary disease, cerebral stroke, diseases relating tissue or organ ischemia, arrhythmia and heart failure. Compound B and A are the preferred and more preferred compounds respectively in the invention.

The compounds of formula (I) exist either in nature or been artificially synthesized. Compounds of formula (I) are screened and evaluated by utilizing the coronary ischemia-reperfusion rat model and the brain ischemia mouse model according to the invention. The major therapeutic and pharmaceutical effects discovered in the invention are the following:

A positive inotropic effect on ischemic heart, increase in left ventricular systolic pressure, maximum changing rate of left ventricular pressure ($dp/dt_{Max}$. mmHg/sec) and contractile function. Histological examination reveals compounds of formula (I) ameliorating the ischemic-reperfusion injury of myocardium and mitochondria, and reducing the size of ischemic infarction area, and preserving the contractile function of the heart under reperfusion. In control group, sever arrhythmia, i.e. ventricular tachycardia and fibrillation occurs in all animals during both periods of ischemic and reperfusion. One third of the animals were dead due to the continuation of ventricular fibrillation. In test group with compounds of formula (I), there is no animal dead as results of arrhythmia. The frequency of occurrence, onset time and duration of ventricular fibrillation are significantly reduced during ischemia and reperfusion. A excellent advantage of compounds of formula (I) is the compounds ameliorating both myocardium ischemia and arrhythmia, while play a significant role in enhancing cardiac contractile function. The said compounds apparently have better therapeutic index over digitalis glycoside which has side effects including pro-arrhythmia and worsening myocardium ischemic. In animal with cerebral ischemia, compounds of formula (I) can protect ischemic brain and significantly prolong its function. According to the invention, kaurene compounds of formula (I) can be use as therapeutic medication for following clinic aspects: in treatment and prevention of ischemic heart disease (coronary disease) such as angina pectoris and acute cardiac infarction; in treatment and prevention of decrease in cardiac function or heart failure (i.g. congestive heart failure) as a positive inotropic agent; in treatment and prevention of arrhythmia such as ventricular tachycardia or fibrillation; in treatment and prevention of cardiac or cerebral reperfusion injury; in treatment and prevention of ischemia stroke, hemorrhagic stroke and other cerebral vascular diseases as well as cerebral injury or dysfunction caused by shock or head trauma; in treatment and prevention of ischemic injuries of extremity of limbs, retina and optic nerves or kidneys.

The therapeutic effects of compounds of formula (I) are dose-dependent within a certain dose range. In general, the potency of compound A is higher than compound B.

Compounds of formula (I) including compound A and B can form pharmaceutical acceptable salts with other material such as basic metals (e.g. sodium) and halogen. They can be combined with pharmaceutical carriers to formulate pharmaceutical compositions. Compounds of formula (I) and their pharmaceutical compositions can be administered by oral, intravenous or other routes, and administered by catheter intervention into veins and arteries.

There is a lack of clinically wide acceptable medications in art with high efficacy and low toxicity in treatment of coronary disease, brain stroke, heart failure and arrhythmia. In light of this shortcoming, the invention discloses a more desirable medication with high efficacy and less adverse effects from the low bio-toxic kaurene compounds. The said compounds are better therapeutic medication than what that in art in treatment of coronary disease, brain stroke, heart failure and arrhythmia. Studies on kaurene compounds in the prior art have neither utilized the similar animal models and experiment protocols, nor reported the similar findings as did in this invention. The invention first demonstrates the effects of kaurene compounds on the ultra-structure of cardiac myocytes. The invention reveals a maximum efficacy and potency of the said compounds in vivo, which are higher than what that ever been reported in the prior art. Further, the said compounds of the invention show a better therapeutic index than the commonly used digitalis in treatment of heart failure and arrhythmia. It is apparent that the invention discloses a novel therapeutic use of kaurene compounds, and this discovery is of non-obviousness.

Above is a general description of the invention. The methods and technologies according to the invention are better illustrated by the following examples, so that they can be performed by a skilled person in art.

The methodologies and embodiments of this invention are provided in detail in the following examples.

EXAMPLES

To further illustrated the technologies used to achieve the objects of the invention, a detailed methods, techniques, procedures, and special features regarding in determining and identifying the pharmaceutical and therapeutic usefulness of kaurene compounds in this invention are described bellow.

Examples provide experimental methods and results which are utilized for supporting the invention, and for validating the animal models used in the invention. Proper control and statistic testing are used in all the experiments in this invention. The following examples are provide to illustrate, not limit, the invention. The examples illustrate the methods and techniques utilized to screen and to determine the therapeutic use of some kaurene compounds in the compounds of formula (I). The therapeutic use of other compounds of formula (I) can also be determined in the same way.

Experiment Materials

Animal: Sprague-Dawley rats or mice of both sexes. Chemical: Compound A, (ent-17-norkaurane-16-oxo-18-oic acid, molecular formula, $C_{20}H_{40}O_3$, Molecular weight: 318.5) is produced from stevioside through acidic hydrolysis, crystallization and purification. The structure of compound A are confirmed by inferred analysis and NMR, which are consistence with previously published data. The purity of compound A is greater than 99% determined by high performance liquid chromatograph. Compound B (ent-13-hydroxykaur-16-en-18-oic acid) is produced from stevioside through a series processes including oxidation, hydrolysis, acidification, extraction, purification and crystallization. The structure of compound B is confirmed by inferred analysis and NMR, which are consistence with previously published data. (Mosettig E. et al., 1963). The purity of compound B is greater than 99% as determined by high performance liquid chromatograph. Administration of testing compounds: intravenous or intraperitoneal injection or oral. Dosage: Compound A: 0.5 mg/kg to 4 mg/kg; compound B: 2 mg/kg to 8 mg/kg.

Experimental Methods

1, Measurements of Cardiodynamic Parameters

Rats were anesthetized, the tracheotomy was performed and an intubation cannula was connected to a respirator for artificial respiration. Arterial blood pressure monitored by a pressure gauge via a femoral artery. A Miller pressure gauge was intervened into left ventricular chamber via a carotid artery to monitor ventricular pressure. The pressure gauges were connected to a Power-lab biological real-time data recording system. ECG was monitored and recorded via subcutaneous needle probes on the arms of rats. The parameters recorded including: Mean arterial blood pressure (MAP), left ventricular systolic pressure (LVSP), the first derivatives of left ventricular pressure ($\pm dp/dt_{Max}$), left ventricular diastolic pressure (LVDP), left ventricular end diastolic pressure (LVEDP) and heart rate (HR).

2, Establishment of Cardiac Ischemia-Reperfusion Animal Model

The chest was open by a left-side thoracotomy between the 4th intercostals space. The pericardium was opened to expose the heart. A stainless needle and a silk suture were placed around the left coronary artery (LCD) and a loose snare ligation was formed. After complete the surgery, the animals were allowed to stabilize for 10 minus before the occlusion of LCD by tightening the snare. A success in occlusion was associated with an area of pericardial cyanosis, an elevation of T wave or ST segment in ECG. The ischemia period of occlusion was maintained from 20 or 30 minus. Cardiac reperfusion was then achieved by releasing of the snare and was confirmed by hyperemic blushing of the previous ischemic area of cyanosis and gradually recovery of the changes in ECG signals. The reperfusion period was maintained for 50 to 80 minus. ECG, MAP and other cardiodynamic data were recorded before the ischemia (control), and during the periods of ischemia and reperfusion.

The animal model noted above is well-characterized and has been used over long time in related studies (Liu, Y and J. Downey, 1992).

Period of Ischemia:
the occlusion of LCD coronary results in myocardium ischemia in part of the heart in rats, which is analogous to the symptoms and pathologies of acute cardiac infarction or cardiac ischemia due to coronary disease in clinic.

Period of Reperfusion:
the heart was reperfused following the reopening of coronary by releasing of ligation, which is analogous to the situations of cardiac ischemia-reperfusion seen in clinic. Such as reopen of coronary in angioplasty via catheter intervention, drugs induced or spontaneous thrombolysis, release of coronary spasm, extracorporeal circulation and acute by-pass surgery. The above mentioned clinic situations may result in fast reperfusion of the heart and may lead to myocardium injury and arrhythmia.

3, Experimental Protocol and Animals Grouping

Animal groups: rats were randomly allocated into the following groups. There are 6 to 8 animals (equal in sex) in each group.

Control group: occlusion of coronary/ischemia-reperfusion. Testing group: occlusion of coronary/ischemia-reperfusion plus compound A or B Sham-operated group: non-occlusion of coronary/sham surgery.

| Protocol: | |
|---|---|
| Control group: \| -10 min--- \| ----20 min----- \| -------------50 min------------------- \|<br>i.v Occlusion LCA Release occlusion, reperfusion | (Saline) |
| Testing group: \| -10 min--- \| ----20 min----- \| -------------50 min------------------- \|<br>i.v Occlusion LCA Release occlusion, reperfusion (compound) | (Testing) |

In part of the experiments, the time periods for occlusion and release of coronary were set for 30 min and 80 min, in order to enhance the results of ischemia-reperfusion.

3, Statistical Analysis

Data are reported as mean±SD. t test or paired t test were used between two groups. For comparison of enumeration data, 2×2 contingent test was used.

Example 1

This example illustrates the effects of Compound A in protection and enhancement of ischemic heart function and on cardiodynamic data.

As shown in table 1, In control group, before and after ischemia by occlusion of coronary, there were no significant changes in HR and $-dp/dt_{Max}$, there were a tendency of decease in MAP and increase in LVEDP but no statistic significance (P>0.05). However, LVSP and $+dp/dt_{Max}$, which represent the contractile function of the heart, were significantly decreased after ischemia by occlusion of coronary than before (P<0.01). These results indicate that the contractile function of the heart in control animals were significant decreased during ischemia.

TABLE 1

Cardiodynamic changes before and after ischemia by coronary occlusion and reperfusion (control group, =n8)

| | HR (beat/min) | MAP (mmHg) | LVSP (mmHg) | $+dp/dt_{Max}$.LVSP (mmHg/sec) |
|---|---|---|---|---|
| Before Ischemia | 372 ± 17 | 71 ± 3 | 118 ± 6 | 8704 ± 326 |
| Ischemia | 388 ± 15 | 67 ± 4 | 98 ± 2** | 6472 ± 219** |
| Reperfusion | 389 ± 11 | 62 ± 6 | 107 ± 4* | 6437 ± 395** |

Significant difference comparing before ischemia
*P < 0.05;
**P < 0.01.
$+dp/dt_{Max}$.LVSP: Maximum changing rate in LVSP (left ventricular systolic pressure), MAP: mean arterial pressure, HR: heart rate.

The results in testing group of compound A (1 mg/kg) are different than in control group. As shown in table 2, after ischemia by coronary occlusion all the cardiodynamic parameters including LVSP and $+dp/dt_{Max}$. LVSP were no significant decreases comparing of before. Comparing the results of testing group with control group, the differences indicate that compound A has significant protecting and enhancing effects on the contractile function in ischemic heart.

TABLE 2

Cardiodynamic changes before and after ischemia by coronary occlusion and reperfusion (testing group of compound A, n = 8)

|  | HR (beat/min) | MAP (mmHg) | LVSP (mmHg) | +dp/dt $_{Max}$.LVSP (mmHg/sec) |
|---|---|---|---|---|
| Before ischemia | 367 ± 13 | 73 ± 3 | 111 ± 4 | 8543 ± 486 |
| Ischemia | 375 ± 10 | 70 ± 5 | 103 ± 3 | 7468 ± 558 |
| Reperfusion | 394 ± 7 | 76 ± 3 | 114 ± 5 | 8431 ± 340 |

+dp/dt $_{Max}$.LVSP, Maximum changing rate in LVSP (left ventricular systolic pressure); MAP, mean arterial pressure; HR, heart rate.

Example 2

This example illustrates the therapeutic effects of compound A in treatment of arrhythmia.

Arrhythmia of ventricular tachycardia (VT) and fibrillation (VF) are the main causes of death in clinic. In the control group during ischemia, VT occurred in all of the 11 animals, VF occurred in 10 out of the 11 animals, and 3 out of the 11 animals were dead due to continuation of VF. However, in the testing group treated with compound A, all the animal survived the cardiac ischemia. The results from both control and testing groups during cardiac ischemia including the frequency of occurrence, onset time and duration of the VT and VF are shown in table 3. These results show that in testing group treated with compound A (1 mg/kg), the frequency of occurrence and duration of VT and VF were significantly reduced (p<0.01) and onset time of VT and VF was significant delayed (P<0.01) during ischemic in comparing with control group. These demonstrate that compound A can protect cardiac function by effectively reducing the risk and alleviate the seriousness of lethal arrhythmia including VT and VF.

TABLE 3

The therapeutic effects of compound A and B in treatment of arrhythmia (occlusion of coronary for 20 min)

|  | VT Frq (%) | Duration (sec) | VF Frq (%) | Duration (sec) | VTorVF Onset(sec) | VT + VF score |
|---|---|---|---|---|---|---|
| Control(n = 8) | 8/8 (100) | 34 + 10 | 7/8 (91) | 37 + 11 | 370 + 41 | 107 + 31 |
| Compound A *(n = 7)(1 mg/kg) | 3/7 (43) | 12 + 6 | 1/7 (14) | 1 | 730 + 166 | 14 + 7 |
| Compound B *(n = 7)(2 mg/kg) | 2/5 (40) | 21 + 12 | 1/5 (20) | 1 | 660 + 178 | 22 + 13 |

*Significant difference comparing of control group (P < 0.01), Score of VT + VF = (duration of VT × 1) + (duration of VF × 2). VT, ventricular tachycardia; VF, ventricular fibrillation; Frq. (%), frequency of occurrence in rats within a group.

Example 3

This example illustrates the protective effects of Compound A on the heart during reperfusion after ischemia and the changes of cardiodynamic.

In the control group, during 50 min of reperfusion after reopening of coronary, the cardiac function and cardiodynamic parameters remain decreased as in the period of ischemia. Comparing with period of pre-ischemia, LVSP and +dp/dt $_{Max}$. LVSP, which reflecting the contractile function are significantly reduced (P<0.05 and P<0.01 respectively), although there were no obvious changes in HR, LVEDP, and −dp/dt Max. LVDP. The MAP was somewhat lower but no statistic significance (P>0.05). These results show that in control group, reperfusion results in a decrease in cardiac contractile function as did in ischemia. (also see table 1). However, in the testing group treated with compound A (1 mg/kg), During reperfusion the LVSP, +dp/dt $_{Max}$. LVSP and other cardiodynamic parameters remain unchanged comparing with the period of pre-ischemia. Comparing with ischemic period, the MAP, LVSP and +dp/dt $_{max}$. LVSP show a tendency of increase but no statistical significance (P>0.05). (also see table 2) The above results from both groups indicate that compound A has significant protecting effects on the cardiac contractile function against reperfusion injury.

Example 4

This example illustrates the protecting effects of compound A on limiting infarct size of myocardium during ischemia.

Determination of the infarct size of myocardium: In both control and testing groups, After the end of reperfusion period, the coronary was occluded, Evans blue dye (1%, 0.5 ml) was injected to determine the ischemic and non-ischemic area of myocardium. Subsequently, the heart was excised, frozen, sliced and washed with Tris buffer. The slices were viewed under microscope. The infarct area and the ischemic area (risk zone) were distinguished according to the color stained. After weighing the respective tissue samples, the infarction size of myocardium was calculated and express as following: Size of infarction=weight of infarct tissue/(weight of infarct tissue+weight of ischemia tissue) x %.

Results: The size of infarction after ischemia were 58.6±4.7% in control group, and 45.8±2.9% in testing group treated with compound A (1 mg/kg). Significant difference is found between groups (P<0.01). This indicates that compound A has protective effects on limiting infarction size of ischemia myocardium.

Example 5

This example illustrates the protective effects of compound A on the morphology of ischemic myocardium At the end of experiments, the ischemic and non-ischemic normal myocardium were excised at the ischemic region respectively from both control or testing groups (compound A 1 mg/kg), and from sham-operated animals at respective region of the heart. The tissues were fixed with paraformaldehyde, embedded in wax, cut into thin or ultra-thin sections, stained and viewed under light or electron microscope.

Examined under Light microscope: The tissue slices were examined under 100× microscope. In non-ischemic cardiac myocyte, striate of myocardium are clearly evident; tight inter myocytes space without sign of either edema or inflammatory. In ischemia myocytes, the normal striates were disappeared, vacuolar degeneration was found within the myocytes. Large inter myocytes space was found with edema and inflammatory cell infiltrating. Destruction of myocytes was evident. In testing group treated with compound A, Striates are visible. No vacuolar degeneration was observed. Inter myocyte spaces were normal and inflammatory cells found only occasionally. Destruction of myocytes was not evident.

Examination under electron microscope: The ultra-thin stained sections were examined under transmission electron microscope, magnitude of ×12000. In non-ischemic myocyte, membranes of both myocytes and mitochondria were intact. Within mitochondria, crestae were dense, matrix and granules are normal distributed. In ischemia control group, cellular membranes were broken. Mitochondria were swollen with broken membrane. There were loss of matrix and large vacuoles within mitochondria and the crestae were reduced in numbers, disorganized and disrupted. The damage of mitochondria is evident comparing to normal. In testing group with compound A, Both membrane of myocytes and mitochondria were intact. The densities of crestae and matrix or the distribution of granules appear normal. There were no observable damages of the myocytes and mitochondria comparing with non-ischemia myocytes, Histological examination shows significant protective effects of compound A on myocardium by alleviating the ischemic damage of myocytes and mitochondrial, Examples 6 to 8 illustrate the pharmaceutical and therapeutic uses of compound B.

Example 6

This example illustrates the protective effects of compound B on the morphology of ischemic myocardium caused by coronary occlusion.

Compound B is an isomer of compound A. This example illustrates the protective effects of compound B on the morphology of ischemic myocardium.

Analogously to Example 5 except the testing group treated with compound B (2 mg/kg). Myocardiac tissues from non-ischemia, ischemia and testing group animals were excised and prepared as noted above. Myocytes and its ultra structure were examined under light and transmission electron microscope. The results show that in testing group treated with compound B, both the myocytes and mitochondria membrane were intact. The densities of crestae and matrix appear normal, and the granules normally distributed within mitochondria. Damages of both myocytes and mitochondria were not evident in comparing with non-ischemia myocytes. The histological results were similar to the results from the animal treated with compound A (1 mg/kg) and indicate significant protective effects of compound B on myocardium by alleviating the ischemic damage of myocytes and mitochondria.

Example 7

This example illustrates the therapeutic use of compound B in treatment of arrhythmia during cardiac ischemia.

Analogously to Example 2 the therapeutic use of compound B in treatment of arrhythmia was studied. The results are the following: (also see table 3 in example 2). In control group, ventricular tachycardia occurs in all of 11 animals, 3 out 11 animals are dead due to the continuation of ventricular fibrillation. However, in testing group (n=5) treated with compound B (2 mg/kg), none of the animals are dead during cardiac ischemia. In comparing of the control, the occurrence and duration of ventricular tachycardia and fibrillation are significantly reduced during cardiac ischemia (P<0.01), their onset time were also significantly delayed (P<0.01). In addition, in term of the therapeutic effects on arrhythmia, the effectiveness of compound B of 2 mg/kg is similar to compound A of 1 mg/kg according to the results (see table 3 in example 2). This indicates that compound A is more potent than compound B.

Example 8

This example illustrates the therapeutic use of compound B in enhancing cardiac contractile function during ischemia.

Analogously to Example 1, the therapeutic use of compound B was studied. The results were following: In control (ischemia) group, Left ventricular systolic pressure (LVSP) and its maximum changing rate (+dp/dt$_{Max}$.LVSP) are 118±6 mmHg and 8704±326 mmHg/sec respectively before ischemia; are 98±2 mmHg 和 6472±219 mmHg/sec, respectively during ischemia. LVSP and +dp/dt$_{Max}$. LVSP are 107±4 mmHg and 6437±395 mmHg/sec respectively during reperfusion. The LVSP and +dp/dt$_{Max}$. LVSP during ischemia and reperfusion are significantly decreased comparing with the same values before ischemia. (P<0.01). These show that ischemia and reperfusion results in a significant decrease in cardiac contractile function in control (ischemia) group.

On the other hand, in testing group treated with compound B (2 mg/kg), They LVSP and +dp/dt$_{Max}$. LVSP are 112±5 mmHg and 8609±543 mmHg/sec. before ischemia respectively; are 104±4 mmHg and 7592±433 mmHg/sec. respectively during ischemia; and are 110±4 mmHg and 8362±498 mmHg/sec. respectively during reperfusion. The LVSP and +dp/dt$_{Max}$. LVSP during ischemia and reperfusion are similar to the same values before ischemia (P>0.05). These results indicate the cardiac contractile function remains unchanged during ischemia and reperfusion in animals treated with compound B.

The above results indicate that compound B can significant protecting cardiac against ischemia and enhance the contractile function during ischemia.

It is evident that the effects of compound B are similar to compound A in the aspects such as, improving ischemic cardiac contractile function, protecting or ameliorating ischemia and reperfusion injuries, alleviating arrhythmia induced by ischemia and reperfusion. In general, compound A has higher potency than compound B.

Example 9

This example illustrates that stevioside has no similar therapeutic effects as note-above in the invention.

Analogously to Example 1, the therapeutic effects of stevioside were studied in rats. In testing group treated with stevioside (10 to 15 mg/kg), No significant therapeutic effects on cardiac contractile function or arrhythmia were observed. The results indicate that stevioside per se has no the similar therapeutic effects as compound A or B.

Example 10

This example illustrates the therapeutic effects of compound A or B in treatment of cerebral ischemia.

Brain ischemia animal model and experimental method.

Decapitated mouse model: The mouse first decapitated and the movement of mouth opening was monitored as a sign of respiration. The frequency and duration of mouth-opening was used as an index of cerebral function after decapitation.

The animals were randomly assigned into three groups (n=8, equal number in sex): Control group, only vehicle saline were given; Testing group, compound A (4 mg/kg) dissolved in saline were given; and Positive control group, a reference compound Edaravone (8 mg/kg) dissolved in saline were given, Edaravone is an anti-oxidation drug and has protective effects on neuronal injury (Granl A. et al. 1996).

Vehicle or compounds were administered intraperitonealy 30 minus before decapitation.

Results: In both the testing group of compound A or B and Edaravone group, the frequency and duration of mouth opening after cessation of blood supply by decapitation were significant increased in comparing with the control group. These indicate that compound A and B has therapeutic effects in protection of cerebral and central nerve system against ischemia injury.

The therapeutic effects of compound A (4 mg/kg) or B (8 mg/kg) were similar to Edaravone (8 mg/kg); these results are listed in Table 4.

TABLE 4 the therapeutic effects of compound A and B in treatment of cerebral ischemia

|  | Frequency of mouth-opening | Duration(sec) |
|---|---|---|
| Control | 9.7 ± 1.6 | 10.5 ± 2.9 |
| Compound A, 4 mg | 14.0 ± 3.2* | 22.9 ± 5* |
| Compound B, 8 mg | 12.8 ± 2.7* | 20.1 ± 4.1* |
| Edaravone, 8 mg | 13.1 ± 2.4* | 17.1 ± 4.3* |

Significant difference in comparing with control. $P < 0.05$

Example 11

This example illustrates the methods of preparation of pharmaceutical acceptable salt of compound A or B and their liquid injection form.

Preparation of Liquid Injection Form: Compound a and B are not Readily Dissolved in Water, therefore a water soluble salt need to be formed before preparation of liquid form for parenteral use. The salts can be sodium, potassium or other inorganic salts. A preferred method is to use sodium. The method is the following: A solution of 0.01 mole of NaOH is prepared. The liquid sodium salt of compound A or B was formed by dissolving 1 g of the compound A or B into 10 ml of the above NaOH solution and adjusting the PH to neutral. This liquid sodium salt can be further diluted with sterile water or mixed with pharmaceutical carrier at needed concentration for parenteral administration. It can be stored at room temperature.

Example 12

This example illustrates the preparation of pharmaceutical compositions comprising of compound A for therapeutic uses.

In general, compound A may be used as active ingredient and admixed with different acceptable pharmaceutical carriers. Kaurene compounds including compound A and B may be absorbed via intestine, therefore they can also be used in solid pharmaceutical compositions and administered orally.

Preparation of Solid Form Compositions: Kaurene Compounds in Particular Compound a or B were mixed with a portion of pharmaceutical carriers, such as starch, lactose, sodium carboxyl methylcellulose etc. The mixtures can then be used to form tablets, capsules, granules etc. for oral administration.

Tablets: Compound A is mixed in different portion (1-99%) with proper amount of carrier (starch, lactose, sucrose, dextrin, microcrystalline cellulose); disintegrators (dry starch, sodium starch carboxyl, crospovidon, low substituted hydroxypropyl cellulose (L-HPC) etc. Binders (starches, ethanol, sodium carboxylmethylcellulose, carboxylpropylcellulose, methylcellulose, carboxylpropylmethylcellulose), Lubricants (e.g. magnesium stearate). One of the preferred compositions is: Compound A 2 g; starch 40 g; lactose 45 g, sodium starch carboxyl 10 g; 8% of starch paste and 1% of magnesium stearate in proper amounts. The above powders materials are mixed, granulized, dyed and sieved, and then the mass obtained are pressed into 1000 tablets. Each tablet contains 2 mg of compound A.

Capsules: Compound A is mixed in different ratio (1-99%) with proper amount of carrier and lubricants above mentioned, filled into capsules. One of the compositions is: compound A 2 g, starch 200 g; mixed and filled into 1000 capsules. Each capsule contains 2 mg of compound A. Compound A may also mixed with different solvents to form soft capsules.

Controlled or sustained released tablets or capsules: According to method of preparing tables and capsules abovementioned, controlled and sustained release dosage forms of compound A can be prepared by admixed with other pharmaceutical recipients (i.e. macropolymores) as matrix, or by coating the tablet with delivering inhibitors or with semipermeable membrane forming an osmotic pump, by using microcapsules made of semi-permeable membrane, or by combine with liposome. These dosage forms can be administered orally to extend the release and action time of compound A.

Parenteral injection liquid composition: A parenteral liquid composition comprises compound A (portion from 1-90%) in sterile aqueous and pharmaceutically acceptable base. The mixed solution is adjusted for PH, stabilized, filtered, sterilized and bottled for parenteral injection or infusion. One of the compositions is the following: compound A, 2 g, $NaHCO_3$, 2 g, dissolved in 1000 ml sterile water; the solution is adjusted for PH, filtrated, sterilized and then bottled in 2 ml or 5 ml bottle, so each contains compound A for 4 mg or 10 mg respectively. These liquid forms of compound A are used for parenteral injection or infusion.

Other pharmaceutical compositions: Compound A can form into other pharmaceutical compositions such as suppository, ointment, trans-dermal patch or pastille etc.

The abovementioned examples are preferred embodiments of this invention, but do not limit the invention in any way. It is obvious that all the modifications or rearrangements to these examples may be made by any technical persons skilled in art according to what have been disclosed by the invention. These modifications and rearrangements shall be included within the same scope of the invention.

INDUSTRY APPLICATION

The invention relates to use of kaurene compounds in manufacture of pharmaceutical drugs for treatment and prevention of coronary disease, arrhythmia and etc. As demonstrated in animal model, the invention also relates to use of the said compounds in manufacture of pharmaceutical drugs for protection and preserving the cerebral function during cerebral ischemia or stroke.

What is claimed is:

1. A method for treating arrhythmia, brain stroke, heart failure, or reperfusion injury, or for enhancing cardiac contractile function, or for reducing a risk of ventricular tachycardia or fibrillation, comprising administering a compound of formula (I) to a non-diabetic patient in need thereof:

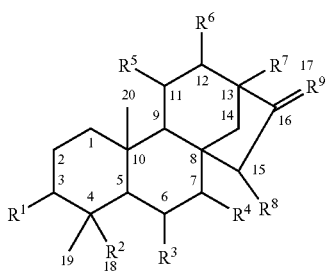

(I)

wherein,
- $R^1$: hydrogen, hydroxyl or alkoxy,
- $R^2$: carboxyl, carboxylate, acyl halides, aldehyde, hydroxylmethyl (—CH$_2$OH), and carboxyl ester, or acylamide,
- $R^3$, $R^4$, $R^5$, $R^6$, $R^8$: independently, hydrogen, hydroxyl, hydroxylmethyl (—CH$_2$OH), or CH$_2$O—R', wherein R' is an acyl or an alkyl,
- $R^7$: Methyl, hydroxyl, or —CH$_2$O—R', wherein R' is an acyl or an alkyl,
- $R^9$: Methylene or oxygen.

2. The method of claim 1, wherein the reperfusion injury is induced by a procedure consisting of coronary angioplasty, thrombolytic therapy, use of a coronary dilation drug, extracorporeal circulation in cardiac surgery, or cerebral thrombolytic therapy.

3. The method of claim 1, wherein, the heart failure is cardiac failure or congestive cardiac failure induced by decreases in cardiac contractile function and cardiac output.

4. The method of claim 1, wherein the arrhythmia is induced by myocardium ischemia and reperfusion injury.

5. The method of claim 1, wherein the arrhythmia is selected from the group consisting of ventricular, super ventricular and atria arrhythmia according to its anatomic and physiological origin.

6. The method of claim 1, wherein the arrhythmia is selected from the group consisting of ventricular tachycardia or ventricular fibrillation.

7. The method of claim 1, wherein, said compound of formula (I) is a compound of formula (II)

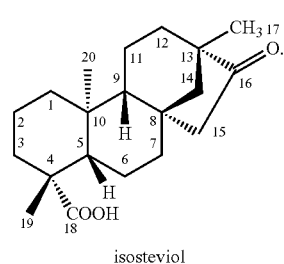

(II)

isosteviol

8. The method of claim 1, wherein, said compound of formula (I) is a compound of formula (III)

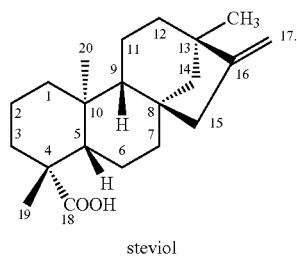

steviol

* * * * *